Figure 1:
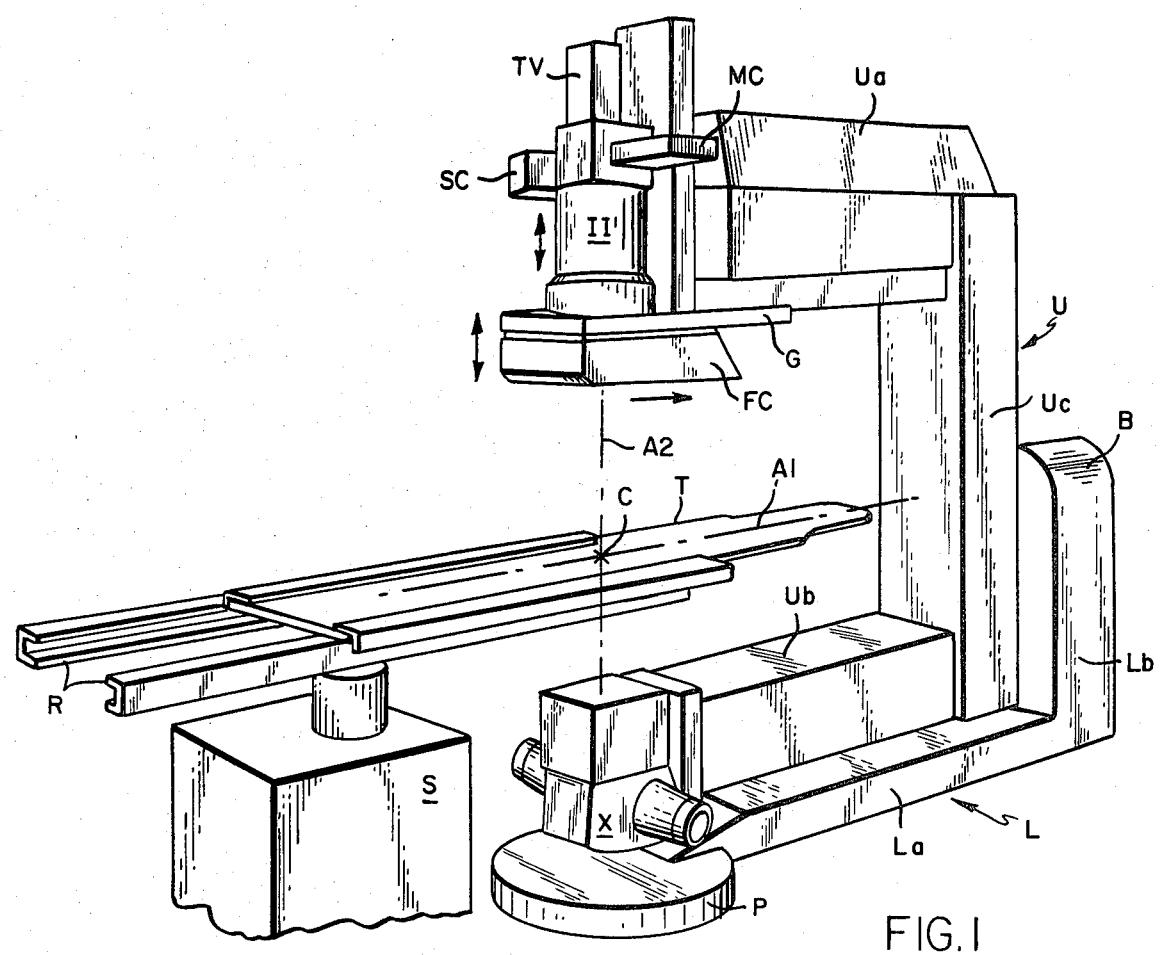

United States Patent [19]

Grady et al.

[11] 4,363,128

[45] Dec. 7, 1982

[54] X-RAY DRIVE APPARATUS

[75] Inventors: John K. Grady, 277 Baker Ave., Concord, Mass. 01742; Paul G. Rice, Lincoln, Mass.

[73] Assignee: John K. Grady, Lincoln, Mass.

[21] Appl. No.: 191,532

[22] Filed: Sep. 29, 1980

[51] Int. Cl.³ ............................................. G03B 41/16
[52] U.S. Cl. ................................... 378/181; 378/189; 378/197
[58] Field of Search ............... 250/439 R, 445 R, 446, 250/447, 448, 449, 490, 491, 523, 468

[56] References Cited

U.S. PATENT DOCUMENTS 3,803,418  4/1974  Holstrom ........................... 250/490
3,833,813  9/1974  James ................................. 250/523

Primary Examiner—Craig E. Church
Attorney, Agent, or Firm—James H. Grover

[57] ABSTRACT

An X-ray apparatus has a moveable support on which are slidingly mounted an X-ray tube, an image intensifier and a film holder, these radiation components defining a common radiation axis. By including a reversible motor connected to a system of clutch operated drive linkages the X-ray tube and receptors can be selectively and reciprocally moved along the radiation axis in either an independent or interdependent manner so as to preserve a radiologically desirable Source to Image Distance (SID) while simultaneously accommodating other X-ray examination requirements such as patient comfort, safety, and desired examining position. The X-ray tube is attached to a lever arm and the image intensifier and film holder are each moved by respective cables travelling around respective drive pulleys and idler pulleys. Both the X-ray tube and receptors are closely counterbalanced by counterweights respectively moved by the cables. When the drive motor is appropriately engaged, a connecting shaft, belt or sprocket chain transmits the motor's force selectively through intermediate, force limited, slip clutches to the appropriate X-ray components.

10 Claims, 2 Drawing Figures

X-RAY DRIVE APPARATUS

BACKGROUND OF THE INVENTION

X-ray apparatus comprises an X-ray tube as a radiation source and one or more radiation receptors such as film holders or changers, image intensifiers, still cameras, motion picture cameras and television cameras. The radiation source and radiation receptor are advantageously mounted on parallel arms of a rotating U-shaped support such as is shown in U.S. Pat. No. 3,892,967, and have a common radiation axis about which the X-rays travel between the X-ray tube and the radiation receptor and on which the radiation source and receptor are centered. The radiation axis passes through a location occupied by a patient or other subject of radiological examination and the image magnification of the subject at the receptor is determined by the distance of the radiation source from the location of the subject. The magnification can be varied by moving the source along the radiation axis but it is highly desirable to maintain a fixed distance along the axis between the radiation source and receptor in order to maintain an optimum balance between image quality which improves with distance and radiation dosage of the patient which should be kept as low as possible by limiting the distance from the source to the image at the receptor. Typically a source to image distance (SID) is about one meter. The distance may be selected by moving either the source or receptor along the radiation axis, and thereafter the selected distance is maintained by moving the source and receptor together the same distance.

It is a main object of the present invention to provide apparatus which can drive a radiation source and one or more radiation receptors both independently and interdependently. A further object is to limit the driving force for the source and receptors to avoid injury to the patient or damage to the apparatus. A further object is to allow manual as well as motor drive of the source and receptors.

SUMMARY OF THE INVENTION

According to the invention radiological apparatus comprises a support; radiation source means and radiation receptor means at spaced positions on the support for examination of a subject at a location therebetween, the source and receptor means having a common radiation axis extending through the subject location, and each means being mounted on the support to move along the radiation axis; a motor, a first drive linkage and a first clutch, the motor being connected by the linkage and clutch to one of the moveable radiation means to drive said one means along the radiation axis; and a cross drive linkage, a second clutch and a second drive linkage forming a drive connection between the first drive linkage and the other radiation means; whereby with either clutch disengaged one of the radiation means is driven independently to select the spacing between the radiation means, and with both clutches engaged both radiation means are driven interdependently so as to vary the radiation image magnification of the subject while maintaining a selected spacing between the radiation means.

Further according to the invention a first motor drives the first linkage to a first radiation means and the apparatus includes a second radiation receptor means mounted on the support adjacent the first receptor means and moveable on the radiation axis, a second motor, a third drive linkage and a third clutch connecting the second motor to the second receptor means for moving the second receptor means independently of the first receptor means and the radiation source means.

Still further according to the invention the first linkage drives a first radiation receptor means and the apparatus includes a second radiation receptor means mounted on the support adjacent the first receptor means and moveable on the radiation axis, a third drive linkage to the second receptor means, and a second cross linkage between the second drive linkage and the third drive linkage for driving the first and second radiation receptor means interdependently.

DRAWING

Figure 2:
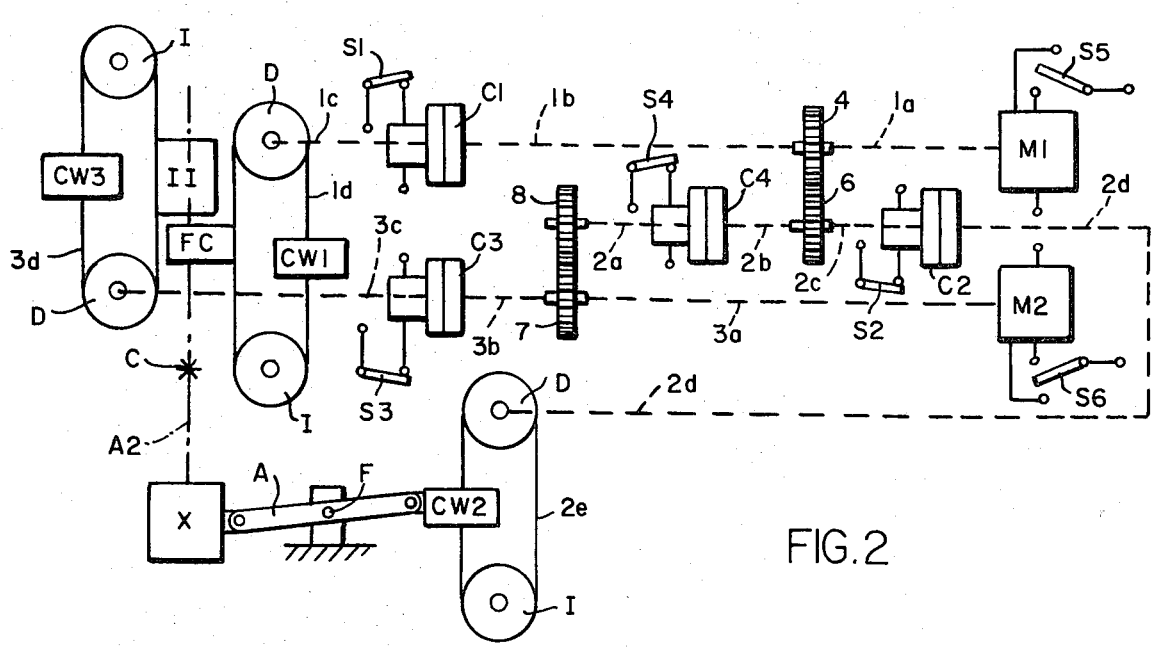

FIG. 1 is an isometric view of X-ray apparatus; and
FIG. 2 is a diagrammatic view of the drive of the apparatus.

DESCRIPTION

The X-ray apparatus in FIG. 1 comprises a support including an L-shaped base L with a horizontal arm La swinging on a pivot assembly P, and an upright arm Lb extending at right angles to the horizontal arm. At the upper end of the upright arm Lb is a heavy bearing B in which a U-shaped part of the support rotates about an axis A1. The U-shaped support part comprises a vertical arm Uc and an upper horizontal extension Ua and a lower extension Ub. At the end of the lower extension Ub is a housing for an X-ray tube X which is a radiation source. At the end of the upper extension Ua is a radiation receptor, a radiation image intensifier II which electronically intensifies the X-ray image and projects the intensified image on a beam splitter allowing the image to be recorded or transmitted by a still camera SC, a motion picture camera MC and a television camera TV. Below the image intensifier II is a radiation receptor such as a film holder or changer FC. The image intensifier II, film changer FC and X-ray tube define a radiation axis A2 which intersects the axis A1 of the U-shaped support part U at an isocenter C. The isocenter C is also the location of the subject of radiological examination. The subject is usually a patient lying on a table T which slides on rails R supported on a standard S.

The radiation source X and the two radiation receptors II and FC are slidingly mounted on the respective extensions Ua and Ub so that they can be moved up and down along the radiation axis A2, as will be described with respect to FIG. 2. The film changer FC can also move transversely of the guides G out of the way of the image intensifier so that either the film changer or image intensifier can be the active radiation receptor. To keep the image intensifier close to the radiation image plane it is desirable to move the image intensifier together with the film changer even though the image intensifier is not active as a radiation receptor.

In FIG. 2 the radiation receptors respectively FC and II are shown carried on cables 1d and 3d travelling around driven pulleys D and idler pulleys I. The receptors are closely counterbalanced by counterweights CW1 and CW3 respectively also carried on the cables. The radiation source X is shown attached to a lever arm A pivotted at a fulcrum F, the other end of the lever arm being attached to a counterweight CW2. The counterweight is carried on a cable 2e travelling around a drive pulley D and an idler pulley I.

The radiation source and receptors are driven by two reversible motors M1 and M2. The first motor M1 is connected to the radiation receptor FC through a first drive linkage 1a, 1b, 1c, a first clutch C1 and the cable 1d. The linkage may constitute any common drive such as a shaft, a belt, sprocket chain or shaft, or a combination of any of these drive linkages. By appropriate closing of a reversing switch S5 the motor M1 may be driven in either direction and through the linkage described the receptor FC is raised or lowered along the radiation axis A2, it being necessary for the first clutch C1 to be closed by closing of the switch S1, as shown.

The clutch C1 (and additional clutches C2, C3 and C4) are electromagnetic, force limited, slip clutches. When engaged, as shown, such a clutch can transmit a limited torque force. For the present X-ray apparatus a preferred force is 10 to 15 pound-feet. A suitable clutch is Model CT-20 manufactured by Kenematsu-Gosho (U.S.A.) Inc. South Plainfield, N.J. While in FIG. 2 all switches are shown closed and the clutches engaged, in operation one or more clutches may be disengaged.

A first cross drive linkage comprising spur gears 4 and 6 connects the first drive linkage to a second drive linkage 2c, 2d and 2e connected through a second step clutch C2 to the lever arm A pivoted to the radiation source, X-ray tube X. When clutch C1 only is engaged, only the radiation receptor FC is moved. When clutch C2 only is engaged, only the radiation source X is moved. When both clutches C1 and C2 are engaged both the radiation source X and receptor FC are moved along the radiation axis A2 simultaneously the same distance in the same direction. All linkages between the motors M1 and M2 and the radiation means FC, II and X have the same drive ratio so that any two or three of the radiation means are always driven the same distance in the same direction.

A second reversible motor M2 is connected to a third drive linkage 3a, 3b, 3c and 3d and a third clutch C3 engaged by a switch S3. This drive linkage connects the second motor M2 to the second radiation receptor, image intensifier II, and when the third clutch C3 only is engaged the image intensifier only is moved along the radiation axis in a direction selected by a reversing switch S6 for the second motor.

A second cross drive linkage comprising two spur gears 7 and 8 links the second drive linkage section 2a to the third drive linkage sections 3a and 3b. When the second and third clutches C2 and C3 only are engaged the second motor M2 drives the second radiation receptor II and the source X interdependently the same distance and direction.

Both radiation receptors may be driven interdependently by engaging a fourth clutch C4 interconnecting the two cross drive linkages 4, 6 and 7, 8.

All of the radiation means FC, II and X may be moved interdependently the same distance and direction by engaging all of the clutches C1, C2, C3, C4 and energizing either one of the reversible motors M1 or M2.

Moving both radiation receptors Fc and II interdependently with or without movement of the radiation source X avoids collision of the two receptors. The linkage system also allows any one of the radiation means to be moved independently for selecting the source to image distance (SID), while allowing the source and either or both receptors to be moved interdependently to maintain the SID constant. The use of counterweights and force limited clutches eliminates the need for complicated sensing system to prevent patient injury since the clutches can transmit only a moderate force to the receptors FC and II which might contact the patient. Rotation of the U-shaped support U may bring one of the radiation means into interference by the patient or table T. But interdependent movement of the radiation means will avoid such interference while maintaining the SID and magnification constant. By energizing only one motor at a time to drive two or three of the radiation means equality of movement of the driven means is insured regardless of speed, starting and stopping forces or voltage variations.

It should be understood that the present disclosure is for the purpose of illustration only and that this invention includes all modifications and equivalents which fall within the scope of the appended claims.

We claim:

1. Radiological apparatus comprising:

a support;

radiation source means and radiation receptor means at spaced positions on the support for examination of a subject at a location therebetween, the source and receptor means having a common radiation axis extending through the subject location, and each means being mounted on the support to move along the radiation axis;

a motor, a first drive linkage and a first clutch, the motor being connected by the linkage and clutch to one of the moveable radiation means to drive said one means along the radiation axis;

a cross drive linkage, a second clutch and a second drive linkage forming a drive connection between the first drive linkage and the other radiation means; and means for selectively engaging the respective clutches so that with either clutch disengaged one of the radiation means is driven independently to select the spacing between the radiation means, and with both clutches engaged both radiation means are driven interdependently so as to vary the radiation image magnification of the subject while maintaining a selected spacing between the radiation means.

2. Apparatus according to claim 1 wherein a first motor drives the first linkage to a first radiation means, and including a second radiation receptor means mounted on the support adjacent the first receptor means and moveable on the radiation axis, a second motor, a third drive linkage and a third clutch connecting the second motor to the second receptor means for moving the second receptor means independently of the first receptor means and the radiation source means.

3. Apparatus according to claim 1 wherein the first linkage drives a first radiation receptor means, and including a second radiation receptor means mounted on the support adjacent the first receptor means and moveable on the radiation axis, a third drive linkage to the second receptor means, and a second cross linkage between the second drive linkage and the third drive linkage for driving the first and second radiation receptor means interdependently.

4. Apparatus according to claim 2 wherein the first linkage drives a first radiation receptor means, and including a second radiation receptor means mounted on the support adjacent the first receptor means and moveable on the radiation axis, a third drive linkage to the second receptor means, and a second cross linkage between the second drive linkage and the third drive linkage for driving the first and second radiation receptor means interdependently.

5. Apparatus according to claims 3 or 4 including a clutch between the first and second cross linkage means.

6. Apparatus according to claims 3 or 4 including a fourth clutch between the second cross linkage and the second radiation receptor means.

7. Apparatus according to any one of claims 1 to 4 wherein each clutch is a force limited slip clutch.

8. Apparatus according to claim 3 wherein one radiation receptor means is moveable transversely of the radiation axis out of the path on the radiation axis of the other receptor means.

9. Apparatus according to claim 1 wherein the support comprises a U-shaped structure having a central rotatable portion and extensions from said central portion to the radiation means.

10. Apparatus according to claims 1 or 3 wherein the drive linkages to the radiation means include counterweights for the respective radiation means.

* * * * *